US00PP28733P2

(12) United States Plant Patent
Noodelijk

(10) Patent No.: US PP28,733 P2
(45) Date of Patent: Dec. 5, 2017

(54) ***CHRYSANTHEMUM* PLANT NAMED 'FIREGLOW'**

(50) Latin Name: *Chrysanthemum morifolium*
Varietal Denomination: FIREGLOW

(71) Applicant: Robert Noodelijk, Woubrugge (NL)

(72) Inventor: Robert Noodelijk, Woubrugge (NL)

(73) Assignee: Floritec Breeding B.V. (NL)

( * ) Notice: Subject to any disclaimer, the term of this patent is extended or adjusted under 35 U.S.C. 154(b) by 0 days.

(21) Appl. No.: 15/330,683

(22) Filed: Oct. 25, 2016

(51) Int. Cl.
*A01H 5/02* (2006.01)

(52) U.S. Cl.
USPC ..... Plt./290

(58) Field of Classification Search
USPC ..... Plt./290, 287, 289
CPC ..... A01H 5/0255
See application file for complete search history.

*Primary Examiner* — Kent L Bell
(74) *Attorney, Agent, or Firm* — Cassandra Bright

(57) ABSTRACT

A *chrysanthemum* plant named 'FIREGLOW' is disclosed, characterized by medium blooms colored bronze-yellow with bronze-orange centers, prolific branching, a natural season flowering date near the end of September, a blooming period of 5 to 6 weeks, a rounded plant habit and a spreading growth habit. Plants are useful for outdoor ornamental purposes, and are known commercially as garden mums.

2 Drawing Sheets

Genus and species: *Chrysanthemum morifolium.*
Variety denomination: 'Fireglow'.

BACKGROUND OF THE INVENTION

'FIREGLOW' is a product of a breeding and selection program for outdoor pot mums (garden mums) which had the objective of creating new *chrysanthemum* cultivars with a decorative type inflorescence, a natural season flowering date around September 26 and a blooming period of 5 to 6 weeks. The new plant of the present invention comprises a new and distinct cultivar of *chrysanthemum* plant.

'FIREGLOW' is a seedling resulting from an open pollination conducted in December 2012 among groups of un-named and unpatented *chrysanthemum* cultivars maintained under the control of the inventor for breeding purposes. The new and distinct cultivar was discovered and selected as one flowering plant by Robert Noodelijk in a cultivated field in Salem, Mo., during September 2013.

'FIREGLOW' was first asexually reproduced by cuttings at a commercial greenhouse in Salem, Mo., December 2013 and has been asexually reproduced over an approximately two-year period. The new cultivar has been found to retain its distinctive characteristics through successive asexual propagations.

SUMMARY OF THE INVENTION

The following are the most outstanding and distinguishing characteristics of the new cultivar when grown under normal horticultural practices in Salem, Mo.

1. Medium size bronze-yellow inflorescences with bronze-orange centers;
2. Prolific branching; and
3. A Rounded plant habit.

COMPARISON WITH PARENT VARIETIES

The parent varieties are unknown to the inventor, as the new variety resulted from an open-pollination with bulk collected seed.

COMPARISON WITH COMMERCIAL CULTIVAR

'FIREGLOW' differs from the commercial variety 'Katelli' (U.S. Plant Pat. No. 16,674) in that 'FIREGLOW' blooms a little later than 'Katelli'. 'FIREGLOW' achieves a height of approximately 45 cm, compared to 30 cm of a similarly aged plant of 'Katelli'. Additionally, 'FIREGLOW' differs in flower color, flower size and flower shape. 'FIREGLOW' has brighter bronze-yellow flowers with almost orange centers, where 'Katelli' has darker colored almost bronze flowers with dark bronze centers. The flowers of 'FIREGLOW' are larger (about 5.5 to 6.5 cm) than the flowers of 'Katelli' (about 4.5 cm) and the ray florets of 'Katelli' are broader and more rounded than the ray florets of 'FIREGLOW'.

DESCRIPTION OF THE PHOTOGRAPHS

The present invention of a new and distinct variety of *chrysanthemum* is shown in the accompanying photographs, the colors being as nearly true as possible with color photographs of this type. The photographs are of a plant that has been in bloom for approximately 3 weeks at approximately 16 weeks of age.

DESCRIPTION OF THE INVENTION

Figure 1:
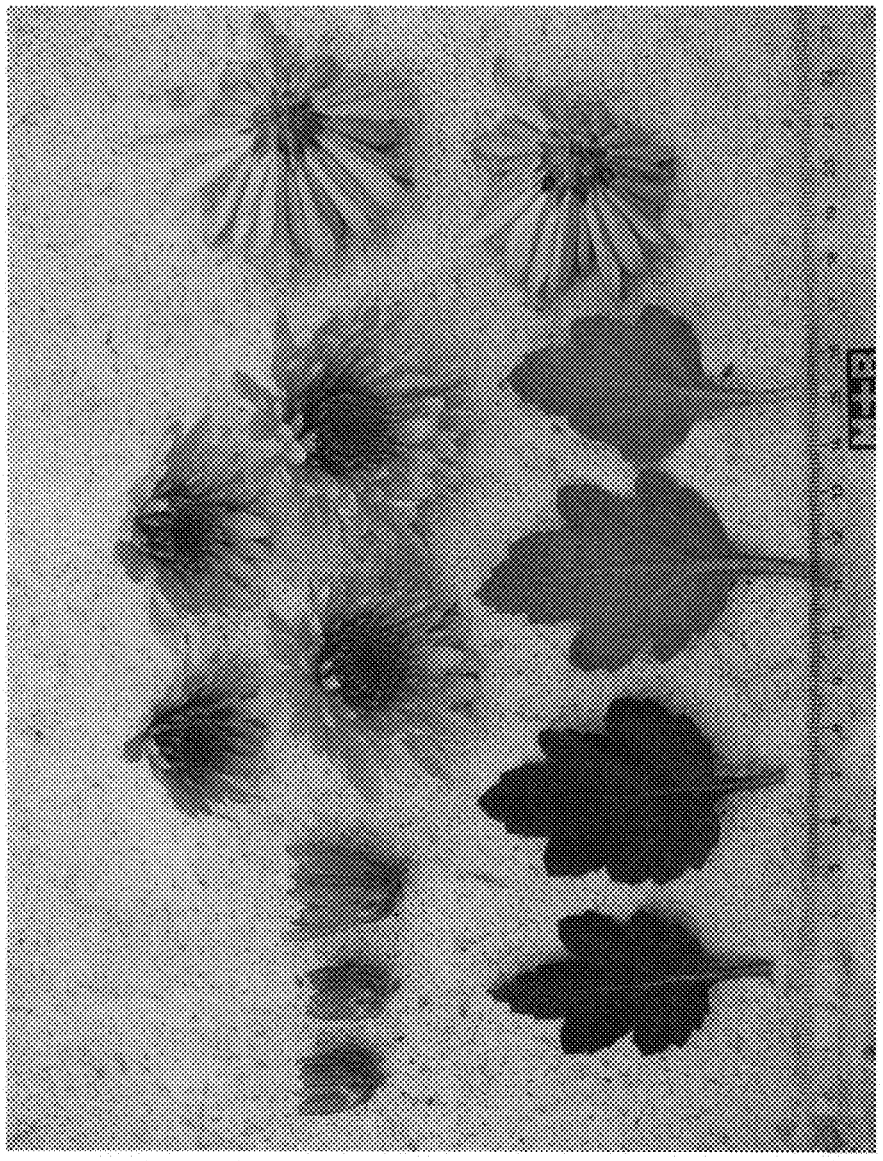
FIG. 1 shows a close-up of the buds, leaves and individual inflorescences.
Figure 2:
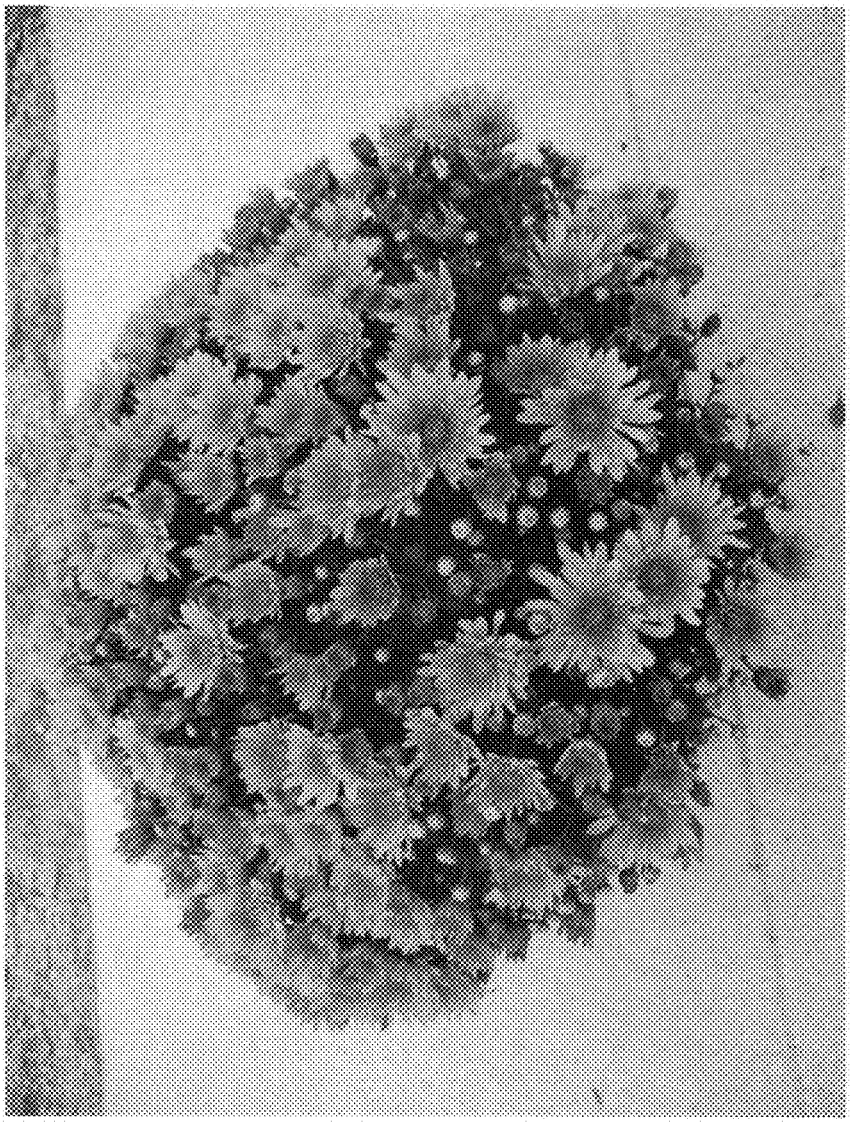
FIG. 2 shows a plant of the cultivar in full bloom.

This new variety of *chrysanthemum* is of the botanical classification *Chrysanthemum morifolium*. The observations and measurements were gathered from plants grown outdoors in Salem, Mo. under natural day length and temperatures and planted in week 22 in 2014 and 2015. The average natural blooming date of this crop was September 26. The average height of the plants was 40 cm to 45 cm. No growth retardants were used. No tests were done on disease or insect resistance or susceptibility. No tests were done on cold or drought tolerance. This new variety produces medium-sized blooms with bronze-yellow florets and bronze-orange centers and a blooming period of 5 to 6 weeks.

The following is a description of the plant and characteristics that distinguish 'FIREGLOW' as a new and distinct variety. The color designations are taken from the plant itself. Accordingly, any discrepancies between the color designations and the colors depicted in the photographs are due to photographic tolerances. The color chart used in this description is The Royal Horticultural Society colour chart, edition 1995.

DETAILED BOTANICAL DESCRIPTION

Classification:

*Botanical.*—*Chrysanthemum morifolium.*

*Common name.*—Garden mum.

*Denomination.*—'FIREGLOW'.

Plant:

*Shape.*—Rounded.

*Growth habit.*—Tender Fall blooming perennial.

*Growth rate.*—Moderate.

*Height.*—40 cm to 45 cm.

*Width.*—40 cm to 50 cm.

Branches:

*Color.*—RHS Green 139C.

*Strength.*—Strong.

*Brittleness.*—Branches are not brittle.

*Anthocyanin coloration.*—Absent.

*Length of lateral branch.*—10 cm to 15 cm.

*Diameter of lateral branch.*—0.7 cm.

*Lateral branch color.*—RHS 138B (Green).

*Average number of lateral branches.*—Prolific with 9 to 11 breaks after pinching.

*Side branches on the laterals.*—Length: 6 cm to 12 cm. Diameter: 0.2 cm. Color: RHS Green 138B. Number: 5-7.

Leaves:

*Color.*—Upper surface: RHS 137A (Green). Lower surface: RH 138B (Green).

*Size.*—General: Medium. Length: 4.0 cm to 5.5 cm. Width: 3.0 cm to 4.0 cm.

*Quantity* (*fully grown leaves per lateral branch and its side branches*).—6 to 13.

*Shape.*—Ovate.

*Apex.*—Acute.

*Base.*—Asymmetric.

*Margin.*—Lobed and moderate crenate.

*Texture.*—Upper surface: Glabrous. Lower surface: Pubescent.

*Venation arrangement.*—Pinnate.

*Shape of base of sinus between lateral lobes.*—Acute.

*Margin of sinus between lateral lobes.*—Mainly diverging.

Inflorescence:

*Type.*—Decorative.

*Size.*—General: Medium. Fully expanded diameter: 5.5 cm to 6.0 cm. Fully expanded depth: About 2.0 cm.

*Number of blooms per branch.*—Approximately 5 to 10 per branch.

*Performance on the plant* (*blooming period*).—5 to 6 weeks, beginning late September.

*Fragrance.*—Typical of chrysanthemum, slight.

*Color.*—Tonality from distance: A rich flowering garden mum with medium bronze-yellow inflorescences with bronze-orange centers.

*Ray florets.*—Texture: Both the upper and lower surfaces are smooth. Number: 150 to 180. Cross-section: Flat to concave. Apex: rounded. Margin: Entire. Length: 2.1 cm to 2.5 cm. Width: 0.5 to 0.6 cm. Color: Upper surface: Immature/inner ray florets: Near RHS Greyed-Orange 169A. Mature/outer ray florets: Near RHS Yellow 14A. Lower surface: Immature/inner ray florets: Near RHS Greyed-Orange 169A. Mature/outer ray florets of the ray-florets: Near Yellow-Orange 16A with a slight pattern of Greyed-orange 168C. Fading to: Outer ray florets fade to yellow 13A, both surfaces, inner ray florets(flower center) remain 169A, both surfaces.

*Disc florets.*—Disc diameter: 0.1 cm to 0.2 cm. Disc length: 0.4 cm. Quantity of disc florets: very few, 10 to 12 per disc, visible only at very late stages of blooming. Shape: Tubular. Color: RHS 151B (Yellow-green). Receptacle shape: Conical and flattened. Color of center of the flower (disc-florets): Immature: RHS 151B (Yellow-green). Mature: RHS 151B (Yellow-green).

*Peduncle.*—Length: 4.0 cm to 10 cm. Diameter: 0.3 cm. Color: RHS 138B (green).

*Bud.*—Size: General/commercial: medium. Cross-section: 0.9 cm to 1.1 cm. Height: 1.4 cm to 1.6 cm. Outside color : RHS Greyed-orange 171A.

*Involucral bracts.*—Involucral bracts: 3 rows, length is 0.9 cm, width is 0.3 cm color near RHS Green 138B.

Reproductive organs: Stamen present in disc florets only.

*Width.*—0.2 cm to 0.3 cm.

*Length.*—About 0.4 cm.

*Stamen color.*—RHS 14A (Yellow-orange).

*Pollen amount.*—Sparse and appears in a very late stage.

*Pollen color.*—RHS 11A (Yellow).

Style: Disc florets only.

*Style color.*—RHS 1A (Yellow-green).

*Style length.*—0.4 cm.

*Stigma color.*—RHS 3A (Yellow-green).

*Stigma width.*—0.25 cm.

*Ovaries.*—Enclosed in calyx.

Other characteristics:

*Fruit/seed set.*—None observed.

*Disease/pest resistance.*—Typical to known *Chrysanthemum* varieties. Neither resistance nor susceptibility to the normal diseases and pests of *Chrysanthemum* have been observed. Pests common to include leaf miner (*Chromatomyia syngenesiae*) and thrips (*Frankliniella occidentalis, Hliothrips haemorrhoidalis*). Typical diseases are *Botrytis* and *Pythium.*

*Temperature tolerance.*—Approximately USDA zones 5 through 9.

*Drought tolerance.*—No tolerance for drought.

What is claimed is:

1. A new and distinct variety of *Chrysanthemum* plant named 'Fireglow' as described and shown herein.

* * * * *